(12) United States Patent
Geisser et al.

(10) Patent No.: US 6,174,442 B1
(45) Date of Patent: Jan. 16, 2001

(54) ADSORBENT FOR PHOSPHATE FROM AN AQUEOUS MEDIUM, PRODUCTION AND USE OF SAID ADSORBENT

(75) Inventors: Peter Geisser; Erik Philipp, both of St. Gallen (CH)

(73) Assignee: Vifor (International) AG, St. Gallen (SE)

( * ) Notice: Under 35 U.S.C. 154(b), the term of this patent shall be extended for 0 days.

(21) Appl. No.: 09/077,944

(22) PCT Filed: Dec. 19, 1996

(86) PCT No.: PCT/EP96/05695

§ 371 Date: Jun. 2, 1998

§ 102(e) Date: Jun. 2, 1998

(87) PCT Pub. No.: WO97/22266

PCT Pub. Date: Jun. 26, 1997

(30) Foreign Application Priority Data

Dec. 19, 1995 (DE) .............................................. 195 47 356

(51) Int. Cl.[7] .................................................. B01D 15/00
(52) U.S. Cl. .................... 210/645; 210/656; 530/415; 530/417; 514/23; 424/647; 71/28; 71/24; 71/59
(58) Field of Search .................................... 210/645, 656; 530/415, 417; 514/23; 424/646; 71/28, 24, 59

(56) References Cited

U.S. PATENT DOCUMENTS

| 4,213,859 | | 7/1980 | Smakman . | |
|---|---|---|---|---|
| 4,542,015 | * | 9/1985 | Smakman et al. | 424/79 |
| 4,581,141 | * | 4/1986 | Ash | 210/502 |
| 4,626,416 | * | 12/1986 | DeVoe et al. | 423/312 |
| 4,749,695 | | 6/1988 | Schwengers . | |
| 4,927,756 | * | 5/1990 | Schwengers | 435/103 |
| 4,970,079 | * | 11/1990 | Hem et al. | 424/646 |
| 5,411,569 | * | 5/1995 | Hjersted | 71/24 |
| 5,514,281 | * | 5/1996 | Boos et al. | 210/645 |
| 5,534,275 | | 7/1996 | Humbert . | |

FOREIGN PATENT DOCUMENTS

| 382 326 | 2/1987 | (AT) . |
|---|---|---|
| 42 39 442 A1 | 6/1994 | (DE) . |
| 0 052 206 | 5/1982 | (EP) . |
| 0 164 657 A2 | 12/1985 | (EP) . |
| 2 387 045 | 11/1978 | (FR) . |
| WO 95/22908 | 8/1995 | (WO) . |

OTHER PUBLICATIONS

Schwertmann et al., "Iron Oxides in the Laboratory, Preparation and Characterizaton", I, Title II, Cornell, R.M. (1991), pp. 64–65, and pp. 95–100.

Baumgartner, et al., "Pharmakologische und galenische Aspekte der Phosphatbinder Aluminium–hydroxid, Calciumcarbonat und Calciumacetat", Dialyse–Journal 37/1991, pp. 2–42.

* cited by examiner

*Primary Examiner*—James H. Reamer
(74) *Attorney, Agent, or Firm*—Pillsbury Madison & Sutro LLP

(57) ABSTRACT

An adsorbent for phosphate from aqueous medium, particularly for inorganic phosphate or phosphate bound to foodstuffs from body fluids or foodstuffs, which contains beta-iron hydroxide stabilized by carbohydrates and/or by humic acid.

14 Claims, No Drawings

ADSORBENT FOR PHOSPHATE FROM AN AQUEOUS MEDIUM, PRODUCTION AND USE OF SAID ADSORBENT

This invention relates to an adsorbent for phosphate from aqueous medium, for example from aqueous solutions. It is particularly suitable as an adsorbent for inorganic phosphate and phosphate bonded to foodstuffs, especially as a preparation for oral application for the prophylaxis and treatment of hyperphosphataemia conditions.

In patients with chronic renal insufficiency, a pathologically increased serum phosphate level occurs due to the decrease in the glomular filtration rate. The secondary hyperparathyroidism which sets in therewith must be considered as one of the causes of the occurrence of renal osteopathy. Attempts are normally made to maintain the phosphate balance in equilibrium by dialysis or by the administration of oral phosphate adsorbers which suppress the resorption of foodstuff phosphates in the gastrointestinal tract, or by the combination of both methods, but with the current state of the art this is either not efficient enough, is not economic, or is burdened with side effects.

Thus, in addition to dialysis encephalopathy syndrome, the aluminium(III) salts which are used as oral phosphate adsorbers cause renal osteopathy and microcytic anaemia. When calcium salts are used, hypercalcaemia frequently occurs, in combination with calcification of the vessels and internal organs and gastrointestinal complaints (Dialysis Journal 37, 1–40 (1991)).

In addition, the use of adsorption materials modified with polynuclear metal oxide hydroxides has been proposed in DE 42 39 442 A1, but the use of the water-soluble iron dextrans and dextrins described therein has the disadvantage that they are resorbable. Complexes which release only a little iron can be produced by the use of crosslinked polysaccharide carriers. The disadvantages of these complexes, which are based on alpha-iron hydroxides, are firstly the high cost of the crosslinked polysaccharide carriers which have to be used, and secondly their phosphate adsorption capacity, which is in need of improvement.

The object of the present invention is therefore to provide adsorbents for phosphate from aqueous medium, particularly from an aqueous solution. In particular, the adsorbents should be suitable for inorganic phosphate and phosphate bonded to foodstuffs from body fluids, chyme and foodstuffs, they should exhibit an improved phosphate adsorption capacity and they should be capable of being produced simply and economically.

It has been shown that this object can be achieved by the adsorbents for phosphate from aqueous medium, to which the present invention firstly relates, which contain polynuclear beta-iron hydroxide stabilised by carbohydrates and/or by humic acid. These adsorbents are particularly suitable for the adsorption of phosphates from aqueous solutions, for example for the adsorption of inorganic phosphates and phosphates bonded to foodstuffs.

Within the scope of the present invention, it has been shown that polynuclear beta-iron hydroxide has a superior phosphate adsorption capacity. However, since polynuclear beta-iron hydroxide ages with a change in structure, it could not hitherto be used for this purpose. It has been found within the scope of this invention that stabilisation can be effected by suitable compounds, particularly carbohydrates and humic acid. Without being tied to any one theory, it is assumed from this that no complex formation occurs with the carbohydrates, however.

The present invention further relates to the process for producing the polynuclear beta-iron hydroxide stabilised by carbohydrates and/or by humic acid, which can be used as an adsorbent or in adsorbents for inorganic phosphate and phosphate bonded to foodstuffs. In the process according to the invention, an aqueous solution of a base is mixed with an aqueous solution of an iron(III) salt containing chloride ions with the formation of a suspension of brown beta-iron hydroxide with a pH higher than 3, for example 3 to 10. The suspension is subsequently allowed to stagnate. In practice, the suspension can be allowed to stand, for example for 1 to 5 hours. It may be stirred briefly now and again during this stage, for example it may be stirred briefly (for example for 10 minutes) at intervals of 10 minutes. The beta-iron hydroxide obtained is washed with water. This can be effected, for example, by decantation, filtration and/or centrifuging. Washing is carried out until interfering anions, for example chloride ions, are removed. A moist product is obtained which is not dried. The moist product is slurried in water. The amount of water is not critical. The procedure employed is preferably such that the iron content of the suspension obtained (calculated as Fe) is up to 6 percent by weight, most preferably 2 to 6 percent by weight.

Sodium carbonate or sodium bicarbonate in aqueous solution may, for example, be used as an alkali metal carbonate or alkali metal bicarbonate solution.

Water-soluble salts of inorganic of organic acids may, for example, be used as the iron(III) salt. Iron(III) chloride is preferred.

The preparation of β-iron hydroxide (akaganeite) is known in principle in the prior art and is described, for example, in the literature reference by U. Schwertmann and R. M. Cornell, "Iron Oxides in the Laboratory", VCH Verlagsgesellschaft mbH, 1991, pages 95–100. For economic reasons, it may be necessary for the industrial production of the adsorption agent containing β-iron hydroxide to precipitate the iron quantitatively at higher pH values. As is described on page 100 of the aforementioned literature reference, ferrihydrite is then also precipitated at the same time. Mixtures of β-iron hydroxide and ferrihydrite such as these can also be used as adsorption agents according to the present invention and the present invention therefore relates to them also.

One or more carbohydrates and/or humic acid are added to the suspension obtained as above. Water-soluble compounds are preferably used. The carbohydrates and/or humic acid may be added in solid form, wherein they can dissolve in the water which is present. However, it is also possible to add aqueous solutions of carbohydrates.

The amount of carbohydrates or humic acid is preferably selected so that at least 0.5 g carbohydrate or humic acid are added per g of iron (calculated as Fe). The maximum iron content should be 40 percent by weight. The maximum content of carbohydrates and/or humic acid is not subject to any limit, and is primarily determined on economic grounds.

Soluble carbohydrates can be used in particular as carbohydrates, such as various sugars, e.g. agarose, dextran, dextrin, dextran derivatives, cellulose and cellulose derivatives, saccharose, maltose, lactose or mannitol.

The adsorption materials comprising insoluble stabilised polynuclear beta-iron hydroxide which are prepared according to the invention have the advantage that in addition to a high phosphate binding capacity they release little iron and are inexpensive to produce.

It may be advantageous and preferable to add one or more calcium salts to the adsorbents according to the invention. Examples of suitable calcium salts include salts of inorganic or organic acids, particularly calcium acetate. The phosphate binding capacity is increased by the addition of the calcium salt, particularly at higher pH values. Adsorbents such as these, which are provided with calcium salts, can be used particularly advantageously at pH values higher than 5, since the full phosphate binding capacity is retained even then.

It has been shown that an addition of from 400 mg to 2 g, for example about 1 g, of a calcium salt, particularly calcium acetate, per g iron, is particularly advantageous.

The adsorbents according to the invention can be formulated for oral application, for example. They can be formulated as such or together with customary drug additives, such as customary carriers or auxiliary materials. Encapsulation may be effected, for example, wherein customary media which are used in the pharmaceutical sector are used as encapsulating media. It is also possible to provide the adsorbents, optionally together with auxiliary materials and additives, as granules, tablets, dragees or contained in sachets, for example. The daily dose of the adsorbents according to the invention is, for example, 1 to 3 g, preferably about 1.5 g of iron.

The adsorbents according to the invention are also suitable for use for the adsorption of phosphate bound to foodstuffs; for this purpose they are admixed with, for example, foodstuffs. Formulations can be prepared for this purpose as described above for drugs, for example.

The invention is explained in more detail by means of the following examples:

EXAMPLE 1

275 g iron(III) chloride solution ($d^{20}$=1.098 g/ml) were added drop-wise, over a period of 30 minutes with stirring (blade stirrer), to 241.5 g soda solution ($d^{20}$=1.185 g/ml). The suspension was allowed to stand for 2 hours. During this period it was stirred for 10 minutes, six times. The resulting suspension was then treated with 300 ml water with stirring, allowed to stand for 1 hour, and then the supernatant liquid was removed by decantation. This procedure was repeated five times.

208.3 g of a suspension with an iron content of 4.8% (determined complexometrically) were obtained.

15 g saccharose and 15 g starch were added to the above 208.3 g of suspension. The suspension was then concentrated at 50° C. in a rotary evaporator and dried at 40° C. under high vacuum.

47.2 g of powder with an iron content of 21.2% (determined complexometrically) were obtained.

EXAMPLE 2

Determination of the binding capacity of the material prepared according to Example 1 for inorganic phosphate from an aqueous phosphate solution: 10 ml sodium phosphate solution (13.68 g/l $Na_3PO_4 \times 12H_2O$) were added to 236 mg of the material prepared according to Example 1 (corresponding to 0.9 mmole iron) (Fe: P molar ratio=1:0.4). After adjusting the pH to 3.0, 5.5 or 8.0, the suspension was allowed to react for 2 hours at 37° C. Thereafter the suspension was centrifuged and the supernatant liquor was removed by decantation. The sample was made up to 25 ml with distilled water and its phosphorus content was determined photometrically by means of a phosphorus-molybdenum test.

TABLE 1

Phosphate binding capacity, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | — | — | 11.16 | 28.43 | 100 |
| 5.5 | 0.78 | 1.99 | 10.38 | 26.44 | 93 |
| 8.0 | 2.9 | 7.39 | 8.26 | 21.04 | 74 |

EXAMPLE 3

Determination of the binding capacity of the material prepared according to Example 1 for inorganic phosphate from an aqueous phosphate solution, analogously to Example 2, but with the addition of 10 ml sodium phosphate solution containing 27.36 g/l $Na_3PO_4 \times 12H_2O$) to 236 mg of the aforementioned material (Fe:P molar ratio=1:0.8).

TABLE 2

Phosphate binding capacity, Fe : P molar ratio = 1 : 0.8

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 1.67 | 4.26 | 9.49 | 24.17 | 85 |
| 5.5 | 2.57 | 6.54 | 8.59 | 21.89 | 77 |
| 8.0 | 4.24 | 10.8 | 6.92 | 17.63 | 62 |

EXAMPLE 4

Determination of the binding capacity of the material prepared according to Example 1 for organic phosphate from an aqueous phosphate solution.

10 ml glycerophosphate solution (11.02 g/l glycerophosphate disodium salt pentahydrate) were added to 236 mg of the material prepared according to Example 1 (corresponding to 0.9 mmole iron) (Fe:P molar ratio=1:0.4). After adjusting the pH to 3.0, 5.5 or 8.0, the suspension was allowed to react for 2 hours at 37° C. Thereafter the suspension was centrifuged and the supernatant liquor was removed by decantation. The sample was made up to 25 ml with distilled water and its phosphorus content was determined gravimetrically after digesting the organically-bound phosphate and precipitating the inorganic phosphate by means of Lorenz reagent.

TABLE 3

Phosphate binding capacity, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 5.69 | 14.50 | 5.47 | 13.93 | 49 |
| 5.5 | 6.70 | 17.06 | 4.46 | 11.37 | 40 |
| 8.0 | 7.81 | 19.90 | 3.35 | 8.53 | 30 |

EXAMPLE 5

Determination of the binding capacity of the material prepared according to Example 1 for organic phosphate from an aqueous phosphate solution:

10 ml phytic acid solution (23.4 g/l phytic acid) were added to 236 mg of the material prepared according to Example 1 (corresponding to 0.9 mmole iron) (Fe:P molar ratio=1:0.4). After adjusting the pH to 3.0, 5.5 or 8.0, the suspension was allowed to react for 2 hours at 37° C. Thereafter the suspension was centrifuged and the supernatant liquor was removed by decantation. The sample was made up to 25 ml with distilled water and its phosphorus content was determined gravimetrically after digesting the organically-bound phosphate and precipitating the inorganic phosphate by means of Lorenz reagent.

TABLE 4

Phosphate binding capacity, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 2.57 | 6.54 | 8.59 | 21.89 | 77 |
| 5.5 | 3.12 | 7.96 | 8.04 | 20.47 | 72 |
| 8.0 | 3.68 | 9.38 | 7.48 | 19.05 | 67 |

EXAMPLE 6

30.0 g saccharose were added to 208.3 g of the suspension prepared according to Example 1. The suspension was then concentrated at 50° C. in a rotary evaporator and dried at 40° C. under high vacuum. The phosphate binding capacity of the resulting material was determined analogously to Example 2:

TABLE 5

Phosphate binding capacity, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | — | — | 11.16 | 28.43 | 100 |
| 5.5 | — | — | 11.16 | 28.43 | 100 |
| 8.0 | 1.12 | 2.84 | 10.04 | 25.59 | 90 |

EXAMPLE 7

30.0 g amylopectin were added to 208.3 g of the suspension prepared according to Example 1. The suspension was then concentrated at 50° C. in a rotary evaporator and dried at 40° C. under high vacuum. The phosphate binding capacity of the resulting material was determined analogously to Example 2:

TABLE 6

Phosphate binding capacity, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 3.46 | 8.81 | 7.70 | 19.62 | 69 |
| 5.5 | 3.91 | 9.95 | 7.25 | 18.48 | 65 |
| 8.0 | 5.36 | 13.65 | 5.80 | 14.78 | 52 |

EXAMPLE 8

30.0 g white dextrin (Amylum, supplied by Blattmann) were added to 208.3 g of the suspension prepared according to Example 1. The suspension was then concentrated at 50° C. in a rotary evaporator and dried at 40° C. under high vacuum. The phosphate binding capacity of the resulting material was determined analogously to Example 2:

TABLE 7

Phosphate binding capacity, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | — | — | 11.16 | 28.43 | 100 |
| 5.5 | 0.11 | 0.28 | 11.05 | 28.15 | 99 |
| 8.0 | 2.9 | 7.39 | 8.26 | 21.04 | 74 |

EXAMPLE 9

30.0 g humic acid (Fluka, Item No. 53860) were added to 208.3 g of the suspension prepared according to Example 1. The suspension was then concentrated at 50° C. in a rotary evaporator and dried at 40° C. under high vacuum. The phosphate binding capacity of the resulting material was determined analogously to Example 2:

TABLE 8

Phosphate binding capacity, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 0.89 | 2.27 | 10.27 | 26.16 | 92 |
| 5.5 | 2.46 | 6.25 | 8.70 | 22.18 | 78 |
| 8.0 | 2.79 | 7.11 | 8.37 | 21.32 | 75 |

EXAMPLE 10

Determination of the binding capacity of commercially available iron(III) oxides for inorganic phosphate from an aqueous phosphate solution:

10 ml sodium phosphate solution (13.68 g/l $Na_3PO_4 \times 12H_2O$) were added to the amount of iron(III) oxide corresponding to 50 mg iron (corresponding to 0.9 mmole iron) (Fe:P molar ratio=1:0.4). After adjusting the pH to 3.0, 5.5 or 8.0, the suspension was allowed to react for 2 hours at 37° C. Thereafter the suspension was centrifuged and the supernatant liquor was removed by decantation. The sample was made up to 25 ml with distilled water and its phosphorus content was determined photometrically by means of a phosphorus-molybdenum test.

TABLE 9

Phosphate binding capacity of analytical grade iron(III) oxide (supplied by Merck, Germany), Fe content 69.2%, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 10.38 | 26.44 | 0.781 | 1.990 | 7 |
| 5.5 | 10.71 | 27.29 | 0.446 | 1.137 | 4 |
| 8.0 | 10.83 | 27.58 | 0.335 | 0.853 | 3 |

TABLE 10

Phosphate binding capacity of iron(III) oxide monohydrate (supplied by Strem Chemicals, USA), Fe content 61.5%, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 9.71 | 24.73 | 1.451 | 3.696 | 13 |
| 5.5 | 10.49 | 26.72 | 0.670 | 1.706 | 6 |
| 8.0 | 10.38 | 26.44 | 0.781 | 1.990 | 7 |

TABLE 11

Phosphate binding capacity of iron(III) subcarbonate (supplied by Lohmann, Germany), Fe content 59.3%, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 8.93 | 22.74 | 2.232 | 5.686 | 20 |
| 5.5 | 9.82 | 25.02 | 1.339 | 3.412 | 4 |
| 8.0 | 10.16 | 25.87 | 1.004 | 2.559 | 3 |

EXAMPLE 11

Determination of the binding capacities of α-, β- and γ-iron oxyhydroxides for inorganic phosphate from an aqueous phosphate solution. The phosphate binding capacity was determined analogously to Example 10:

TABLE 12

Phosphate binding capacity of α-iron oxyhydroxide (goethite), prepared according to U. Schwertmann, R. M. Cornell, Iron Oxides in the Laboratory, VCH Weinheim, 64 (1991), Fe content 59.7%, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 4.352 | 11.09 | 6.808 | 17.34 | 61 |
| 5.5 | 4.464 | 11.37 | 6.696 | 17.06 | 60 |
| 8.0 | 4.576 | 11.66 | 6.584 | 16.77 | 59 |

TABLE 13

Phosphate binding capacity of β-iron oxyhydroxide (akaganeite), prepared according to U. Schwertmann, R. M. Cornell, Iron Oxides in the Laboratory, VCH Weinheim, 95 (1991), Fe content 52.2%, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 4.129 | 10.52 | 7.031 | 17.91 | 63 |
| 5.5 | 4.576 | 11.66 | 6.584 | 16.77 | 59 |
| 8.0 | 4.464 | 11.37 | 6.696 | 17.06 | 60 |

TABLE 14

Phosphate binding capacity of γ-iron oxyhydroxide (lepidocrocite), prepared according to U. Schwertmann, R. M. Cornell, Iron Oxides in the Laboratory, VCH Weinheim, 81 (1991), Fe content 54.4%, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 3.683 | 9.38 | 7.477 | 19.05 | 67 |
| 5.5 | 4.687 | 11.94 | 6.473 | 16.49 | 58 |
| 8.0 | 4.464 | 11.37 | 6.696 | 17.06 | 60 |

EXAMPLE 12

Determination of the binding capacities of stabilised α-, β- and γ-iron oxyhydroxides for inorganic phosphate from an aqueous phosphate solution. Saccharose and starch in a Fe:saccharose:starch weight ratio of 1:1.5:1.5 were added to the iron oxyhydroxides from Example 11.

The phosphate binding capacity was determined analogously to Example 10:

TABLE 15

Phosphate binding capacity of stabilised α-iron oxyhydroxide (goethite), Fe content 20.6%, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 3.906 | 9.95 | 7.254 | 18.48 | 65 |
| 5.5 | 4.018 | 10.23 | 7.142 | 18.20 | 62 |
| 8.0 | 4.241 | 10.80 | 6.919 | 17.63 | 62 |

TABLE 16

Phosphate binding capacity of stabilised β-iron oxyhydroxide (akaganeite), Fe content 17.7%, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 4.018 | 10.23 | 7.142 | 18.20 | 64 |
| 5.5 | 3.906 | 9.95 | 7.254 | 18.48 | 65 |
| 8.0 | 4.018 | 10.23 | 7.142 | 18.20 | 64 |

TABLE 17

Phosphate binding capacity of stabilised γ-iron oxyhydroxide (lepidocrocite), Fe content 20.0%, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 3.683 | 9.38 | 7.477 | 19.05 | 67 |
| 5.5 | 2.790 | 7.06 | 8.370 | 21.32 | 75 |
| 8.0 | 3.683 | 9.38 | 7.477 | 19.05 | 67 |

EXAMPLE 13

Determination of the binding capacity of a mixture of calcium acetate with the material prepared according to Example 1 for inorganic phosphate from an aqueous phosphate solution:

0.96 g calcium acetate (content 93.5–94.5%) were added to 5 g of the material prepared according to Example 1, which had an iron content of 20.4%, and mixed well. The phosphate binding capacity of the resulting material was determined analogously to example 2:

TABLE 18

Phosphate binding capacity, Fe : P molar ratio = 1 : 0.4

| pH | mg phosphorus in the supernatant solution | mg phosphate in the supernatant solution | mg phosphorus adsorbed | mg phosphate adsorbed | Adsorption in % |
|---|---|---|---|---|---|
| 3.0 | 1.339 | 3.41 | 9.821 | 25.02 | 88 |
| 5.5 | 1.339 | 3.41 | 9.821 | 25.02 | 88 |
| 8.0 | 1.12 | 2.84 | 10.04 | 25.59 | 90 |

EXAMPLE 15

The material prepared according to Example 6 was taken into suspension with water, stirred for 30 minutes, centrifuged, and the upper phase was removed by decantation. This was repeated until sugar was no longer detectable in the aqueous phase. In this manner, 1.8% of the saccharose used could still be detected in the preparation after the washing out operation. This corresponded to an Fe:saccharose ratio of 15:1 in the washed material. This showed that the sugar was not bound as a complex.

EXAMPLE 16

For the production of a standard rat fodder with a total phosphorus content of 0.8%, the dry, pulverulent separate constituents were loaded into a cylinder after being intensively mixed throughout and were pressed into pellets. The composition of the fodder by Weender analysis corresponded to the values given in the following Table. The total phosphorus content was distributed as 0.75% organically bound phosphate and 0.05% inorganic phosphate.

In parallel with this production, a second batch of the same starting materials was prepared according to the same recipe; this batch additionally contained 3% wt/wt of the material prepared according to Example 1.

An analysis for available phosphate was performed on both feedstuff batches, after the completion of production and after a storage period of about 2 months. A phosphate content of 0.68%, corresponding to 84.5% of the amount used, was found in the control comprising the product which did not contain a phosphate adsorber; 0.50% was found in the test preparation, corresponding to 62.6% of the amount used.

The difference of 21.9%, corresponding to 1.75 mg P/g fodder, corresponded to a binding capacity of 1.9 mmole P/g adsorber at an adsorber content of 3%.

Results of the Weender feedstuff analysis for the control preparation without adsorber:

| | |
|---|---|
| crude protein | 19.7% |
| crude fat | 3.2% |
| crude fibre | 5.4% |
| crude ash | 6.5% |
| water | 10.9% |
| N - freely extractable | 54.3% |
| Ca content | 1.2% |
| P content | 0.8% |
| Kahl pellet hardness | 17.3 |

What is claimed is:

1. An adsorbent for adsorbing phosphate from aqueous medium, comprising polynuclear beta-iron hydroxide stabilized by at least one member selected from the group consisting of carbohydrates and humic acid.

2. A process for producing the adsorbent according to claim 1, comprising:

mixing an aqueous solution of a base with an aqueous solution of an iron (III) salt containing chloride ions with formation of a suspension with a pH of 3 to 10, allowing the suspension to stand, washing a precipitate obtained with water, suspending the still moist precipitate in water with formation of a suspension with an iron content of up to 6% by weight, and adding at least one member selected from the group consisting of one or more carbohydrates and humic acid in an amount such that a solid obtained contains a maximum of 40% by weight of iron.

3. A process according to claim 2, comprising:

mixing an aqueous alkali metal carbonate or alkali metal bicarbonate solution with an aqueous solution of an iron (III) salt containing chloride ions with formation of a suspension with a pH higher than 6, allowing the suspension to stand, washing precipitate obtained with water to remove the chloride ions present, suspending the still moist precipitate in water with formation of a suspension with an iron content of up to 6% by weight, and adding at least one member selected from the group consisting of one or more carbohydrates and humic acid in an amount such that the solid obtained contains a maximum of 40% by weight of iron.

4. A process according to claim 2, comprising:

using iron (III) chloride as the iron (III) salt.

5. A process according to claim 2, comprising:

using sodium carbonate or sodium bicarbonate as the base.

6. An adsorbent according to claim 1, wherein the stabilized polynuclear beta-iron hydroxide is obtained by a process comprising:

mixing an aqueous solution of a base with an aqueous solution of an iron (III) salt containing chloride ions with formation of a suspension with a pH of 3 to 10, allowing the suspension to stand, washing a precipitate obtained with water, suspending the still moist precipitate in water with formation of a suspension with an iron content of up to 6% by weight, and adding at least one member selected from the group consisting of one or more carbohydrates and humic acid in an amount such that a solid obtained contains a maximum of 40% by weight iron.

7. A process according to claim 2, wherein the carbohydrate comprises saccharose or dextrin or a mixture thereof.

8. An adsorbent according to claim 1, further comprising a calcium salt.

9. A process for using the adsorbent according to claim 1, comprising adsorbing phosphate from an aqueous medium.

10. A process for using the adsorbent according to claim 1, comprising adsorbing inorganic phosphate and phosphate bonded to foodstuffs from body fluids.

11. A process for using the adsorbent according to claim 1, comprising adsorbing inorganic phosphate and phosphate bonded to foodstuffs from gastrointestinal tract contents.

12. A process for using stabilized polynuclear beta-iron hydroxide defined in claim 1, comprising producing adsorbents for inorganic phosphate and phosphate bonded to foodstuffs from body fluids and from gastrointestinal tract contents, simultaneously with intake of food.

13. A process for using the adsorbent according to claim 1, comprising adsorbing inorganic phosphate and phosphate bonded to foodstuffs, from said foodstuffs.

14. A process for using stabilized polynuclear beta-iron hydroxide as defined in claim 1, comprising producing adsorbents for admixture with foodstuffs.

* * * * *